United States Patent [19]

Kaessmann

[11] Patent Number: 4,881,546
[45] Date of Patent: Nov. 21, 1989

[54] WOUND-CLOSURE DEVICE AND METHOD

[75] Inventor: Hans-Jürgen Kaessmann, Norden, Fed. Rep. of Germany

[73] Assignee: Opti-Patents-, Forschungs-und Fabrikations-AG, Riedern-Allmeind, Switzerland

[21] Appl. No.: 133,554

[22] Filed: Dec. 16, 1987

[30] Foreign Application Priority Data

Dec. 16, 1986 [DE] Fed. Rep. of Germany ....... 3642892
Feb. 28, 1987 [DE] Fed. Rep. of Germany ....... 3706599

[51] Int. Cl.4 ..................... A61B 17/08; A61B 17/04; A44B 19/00
[52] U.S. Cl. ............................... 128/335; 128/334 R; 24/381; 24/386
[58] Field of Search ................. 24/381, 386, 384, 399, 24/400, 409, 410, 411; 128/334, 335

[56] References Cited

U.S. PATENT DOCUMENTS

| 2,012,755 | 8/1935 | DeMuth | 24/381 |
| 2,752,921 | 7/1956 | Fink | 128/334 R |
| 3,516,409 | 6/1970 | Howell | 24/386 |
| 3,984,600 | 10/1976 | Kawase et al. | 24/399 |
| 4,222,383 | 9/1980 | Schossow | 128/335 |
| 4,724,586 | 2/1988 | Tsubokawa et al. | 24/384 |

FOREIGN PATENT DOCUMENTS 3444782 6/1986 Fed. Rep. of Germany ...... 128/335

Primary Examiner—Edward M. Coven
Assistant Examiner—Gary Jackson
Attorney, Agent, or Firm—Herbert Dubno

[57] ABSTRACT

A gaping surgical incision can be closed by drawing the edges of the incision toward one another by the application of traction to the wound. Adhesive strips which project beyond support tapes of a conventional garment-type slide fastener stringer are then applied to the skin along the incision and the slider is closed to provide a healing closure for the wound. Spacer strips between the skin and the support tapes are spaced outwardly from the respective coupling elements to define a free space and prevent the wound from contacting the coupling elements or the support tapes.

25 Claims, 4 Drawing Sheets

METHOD OF WOUND CLOSING

WOUND-CLOSURE DEVICE AND METHOD

FIELD OF THE INVENTION

My present invention relates to a device for closing a wound and especially a surgical wound which at least predominantly is linear, and to a wound-closing method which utilizes this device.

BACKGROUND OF THE INVENTION

It has been proposed (see U.S. Pat. No. 3,516,409 and German Pat. 3,444,782) to utilize principles of a slide fastener for the closing of a wound and, in particular, surgical incision which is generally linear.

The term "wound closure" and terms of similar import are used in the sense of the invention to mean that a gaping incision having the edges of the wound normally spread apart, is used to bring those edges into abutting relationship so that there can ensue a wound-knitting or healing procedure. It is not intended to apply to the covering of a wound which is closed by other means and thus the wound-closure device and method of the invention can be used to close a wound without the stitches or clips which have hitherto been necessary and which can be entirely eliminated utilizing the principles of the invention.

While generally the invention should be considered to be compatible to the body of any living subject in which a surgical incision may be made, in the most common case the body will be that of a human patient or an animal under veterinary care.

When a slide fastener is referred to herein, it will be understood that a device is intended which comprises a pair of tapes, generally of fabric or textile material, along juxtaposed edges of which coupling elements can be provided which are capable of mating with one another upon movement of a slider along the coupling elements. The coupling elements can comprise rows of interdigitatable coupling members whose coupling heads fit between one another and can be separated from one another by movement of the slider in the opposite direction.

In the known device which utilizes the principles of such slide fasteners to close a wound and is described in the aforementioned patents, the slide fastener is a specially provided slide fastener with specially designed tapes and which can be distinguished form conventional slide fasteners of types which have been widely used in the textile trades and which can be described as garment-type slide fasteners.

The specially designed tapes of the prior-art slide fastener have adhesive layers applied directly thereto or coated directly thereon.

Such slide fasteners have not gained acceptance in clinical practice because the special fabrication techniques required for these slide fasteners has made them too expensive for use. In addition, the early devices appear to result in some interaction between the coupling elements and the wound edges causing the adhesion of the coupling elements or the tapes to the wound, scarring and imperfect healing.

Furthermore the earlier devices cannot ensure effective draining of wound secretions because of the latter, and because of the intrinsic characteristics of the construction used, the adhesive bond with the skin tends to release prematurely.

If one applies a cover strip over the conventional wound-closing slide fastener, the pressing of the tape or the coupling elements against the wound cannot be prevented and unesthetic scarring can result from the resulting tendency of the wound to grow onto or into the device.

It has been proposed to increase the adhesion of the tape to the skin to provide the tape with a row of needle-like pins which can be pressed into the skin while the slide fastener is open. This of courses discomforts the patient or the animal and can also give rise to visible scarring.

With respect to the method for closing the wound using particular devices of the above-mentioned patents, it may be mentioned that first a wound must have its edges pressed together by hand and then the slide fastener is closed. This is a considerable drawback because even the method of utilizing the conventional slide fastener is awkward.

For all of these reasons, the slide fastener wound closures of the prior art have only been applied in abdominal surgery (see Neue Züricher Zeitung" of Aug. 22, 1984, "Hamburger Abendblatt" of Whitsuntide 1984), and only for the temporary closure of a wound in the case in which reopening may be required, in the case of peritonitis, pancreatic failure or the like. Even in these cases, to ensure the development of the healing process, the wound closure must be effected by the classical stretching or use of clips and thus the prior art device has not been found to be suitable as a substitute for such classical closure methods.

OBJECTS OF THE INVENTION

It is, therefore, the principal object of the present invention to provide an improved method of wound closure which permits a rapid and effective closure of a surgical incision without the drawbacks heretofore encountered and such that the healing process can be effected without the use of stitches or clips.

Another object of this invention is to provide a device for use in this method which overcomes the drawbacks of solid-fastener devices as hitherto utilized in wound closure.

Another object of my invention is to provide a device for the closing of wounds utilizing solid fastener principles but in which the scarring of the wound is excluded, drainage of the wound poses no problem, a secure bond can be effected to the skin of the patient for as long as the device must be used and, in general, so that the device can be utilized to effect a healing process.

SUMMARY OF THE INVENTION

These objects and others which become apparent hereinafter are attained, in accordance with the invention in a slide-fastener device for wound closure which is characterized by the combination of the following features:

(a). The device utilizes a slide fastener stringer which is the conventional garment-type flexible slide fastener stringer with low elongatability support tapes and coupling elements composed of polyester or polyamide which, in the coupling state, are not subject to compression deformation or buckling;

(b). The slide of the tapes and the coupling elements turned toward the wound is held away from the latter by spacer strips which are affixed to the tapes at distances from the coupling elements so that a free space is provided between the spacer strips of a certain width and height sufficient to ensure that neither the tapes nor the coupling elements will contact the edges of the wound which are pulled together by the solid fastener stringer when the latter is closed; and (c). The adhesive means bonding the tapes to the skin of the patient includes at least one adhesive strip overlying a portion of each tape, projecting beyond the tape away from the coupling and of a width including the projecting portions of the adhesive strips sufficient to withstand the wound closing forces applied when the slide fastener stringer is closed, and a layer of hypoallergenic pressure-sensitive adhesive engaging the skin and on the skin side of the adhesive strip over this width.

The use of textile garment-type flexible slide fastener stringers with low elongatability and buckling-resistant coupling elements is indeed a surprising advantage of the invention, which allows the cost of the device to be minimal, since it has long been thought that such commercially available and common slide fastener stringers could not be used for this purpose (see "Surgical Use of Zippers Worries Manufacturer" in China Post, Nov. 8, 1986).

The device of the invention is so applied that the surgical incision should lie as close as possible directly in line with the center line of the slide fastener in the closed state thereof.

Wound-closing forces are uniformly distributed over large areas without any singular points of stress and because the edges of the wound are pressed together uniformly by the slide-fastener action, clean, practically scar-free healing is ensured, especially since the wound cannot grow together with the tape or the coupling elements. The wound edges are found in the free space described previously which permits secretions to drain away without obstruction and permits air access to the wound as is especially advantageous for healing purposes. The free space also ensures that there will not be any growing together of the coupling members and the wound.

The coupling elements can be coated on their underside and indeed separate tapes can be likewise coated, with wound-compatible coatings, e.g. of silicones, which further prevent such growing together and the resulting scarring.

The free space, moreover, ensures that the slider can be shifted parallel to the incision without coming into contact with the wound edges and exacerbating the injury or interfering with the knitting of these edges.

Experimental tests have shown, indeed, that the wound edges grow together in a substantially better manner and with less impediment than is the case with wound-closing clips or stitches.

Preferably, the gaping operation wound, i.e. the surgical incision, is pulled at its ends, e.g. by single-prong needles, apart in the longitudinal direction of the wound to draw the wound edges closer together, whereupon the device of the invention is applied and the slider moved to complete the pressing of the wound edges together. In this sense and using this principle, the slide fastener can be employed to close nonlinear wounds as well.

According to a feature of the invention, the coupling elements used are of the continuous (coil or meander) type being composed of a monofilament of the polyamide or polyester with the thermoplastic monofilament having a thickness of at most 0.5 mm.

While practically any conventional method used in garment-type slide fasteners for securing the coupling elements to the tapes my be employed, it is preferred to join the coupling elements to the tapes by weaving the coupling elements into the tapes as the latter are woven. Such an attachment between the coupling elements and the tapes allows the weaving operation to establish the buckling resistance of the coupling elements and the other advantageous properties of the slide fastener described above. The coupling elements together in the coupled state can have a width of about 5 mm in the preferred construction.

The support tapes can be composed of various materials utilized in the production of slide fastener stringers for textile and garment purposes and preferably materials which are compatible with the principles of the surgical-bandage making action. Preferred are woven support tapes of polyester or polyamide filaments or yarns.

The free space can be defined between edges of the spacer strips which can be located each at a distance from the center line of the coupled coupling elements generally of 4 to 10 mm and preferably about 7 mm. The thickness of the spacer strips which define the free space should be between 0.5 and 1.5 mm, preferably about 1 mm.

In a preferred embodiment of the invention, the free space forming spacers have adhesive layers on the skin side thereof which ensures an optimum ability to close the wound with the slide fastener and maintain the device bonded to the skin.

The closed wound generally issues secretion and one of the advantages of the wound-closing device of the invention is that it permits the continued draining of secretions from the wound area.

The drainage can be promoted, when, in addition to the free space described for such drainage, one or both of the tapes is provided with a drainage means, e.g. in the form of perforations between the coupling element and the respective inner edge of the spacer strip. The perforations can be spaced apart from one another along the device.

It has been found to be advantageous to make the spacer strips which delimit the free space of the wound from an elastic foamed adhesive strip in the form of a microfoam adhesive plaster of a type commonly used for surgical bandages. The microfoam is usually composed of closed polyvinylchloride or polyethylene cells. The adhesive strips for fastening the support tapes along the edges of the wound can also be formed as elastic foam strips, especially in the form of microfoam adhesive plasters.

The adhesive strips can be formed in one piece with the spacer strips and/or can constitute the spacer strips and the foam material strips which contact the skin can and should have extensibility characteristics similar to those of the skin.

It is also possible, according to the invention to provide the adhesive strips which fasten the support tapes along the edges of the wound as the surgical cotton or gauze strips coated with adhesive layers on their undersides and which in the longitudinal direction are of low extensibility but transversely are somewhat extensible or stitchable.

The attached of the adhesive strips to the support tapes can be effected by adhesive bonding, welding and/or by stitch seams or a basting by which the two are held together.

It is desirable, when the wound is closed by closing the slide fastener, to void application of any longitudinal forces to the skin. To this end I can provide at the closed or open end of the slide fastener a retaining loop which can be gripped in a hematostat or other clamp, or in a forceps, while the slider is drawn along the slide fastener, to take up the traction force generated by the closing action and avoid the transfer of this force to the skin of the patient. The transverse forces, of course, are taken up by the adhesive strips.

The support tapes for the slide fastener, in accordance with the present invention, can be planar bands which can lie in a plane and can have the coupling elements disposed on the tops of these bands, i.e. the support tapes can underlie the coupling elements and be provided between the coupling elements and the skin of the patient. It is, however, possible to use so-called covered or invisible slide fastener stringers.

The support tapes can be folded in a U-pattern along longitudinal axes and the thickness resulting from the fold can contribute to or form the spacing defining the free space.

While the advantages of the device of the invention have largely been developed above, it can be noted once again that the device and method of the invention have the advantage that they permit a healing process to ensue with better results than are available with the classical wound closures by stitching or clips. This applies for both gaping wounds and surgically narrow wounds.

In the case of gaping wounds, the wound edges are drawn back as described, by tugging on the ends of the wound.

The device is adhesively bonded to the skin so that the spacing of the wound edge from the edge of the respective spacing strip is approximately half the width of the free space. The slide fastener can be made some 4 cm longer than the wound and applied so that the stringer extends beyond each end of the wound by about 4 cm.

In a nonlinear injury, the wound can be closed by stages with the slide fastener applied again newly from stage to stage as each prior stage partially closes the wound.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
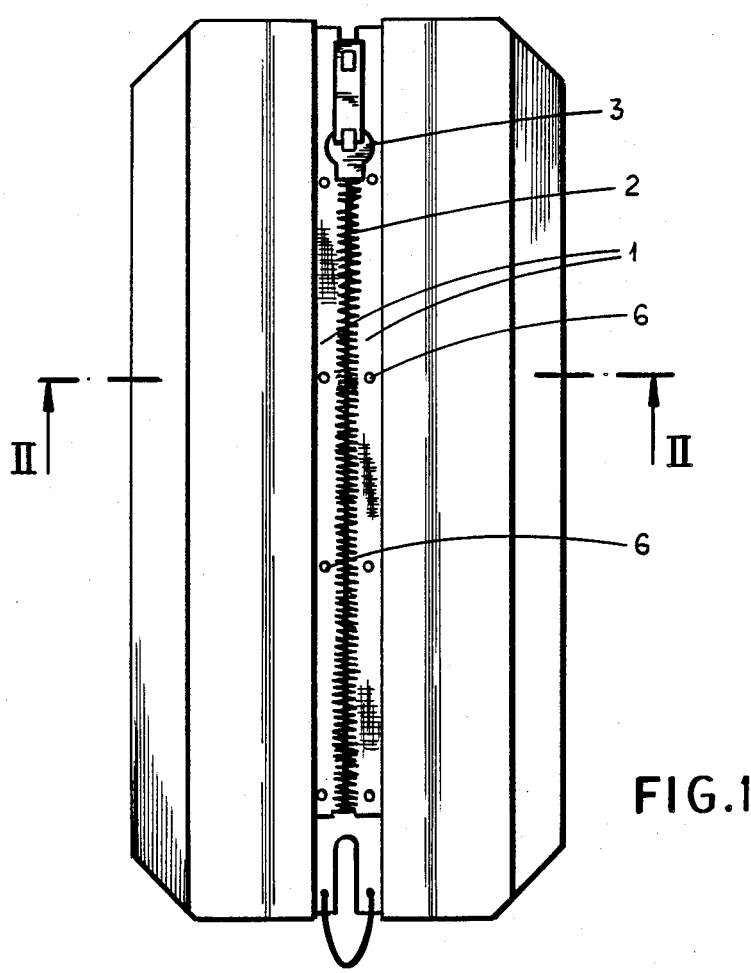
FIG. 1 is a plan view of a device according to the invention as it can be applied to a patient having a surgical incision closed thereby.

The devices shown in the drawing are used primarily to close a wound and especially a linear wound such as a surgical incision. The device basically comprises two textile support tapes 1 and respective coupling elements 2 arrayed juxtaposed edges 1a and 1b of these tapes and forming therewith and with a slider 3 a garment-type slide fastener stringer, in which the heads of the coupling elements can be interdigitated by movement of the slider in one direction along the coupling elements, i.e. upwardly. Means 4 is provided for fastening the tapes 1 to the skin S of a patient or an animal along the edges R of a wound W.

Figure 2:
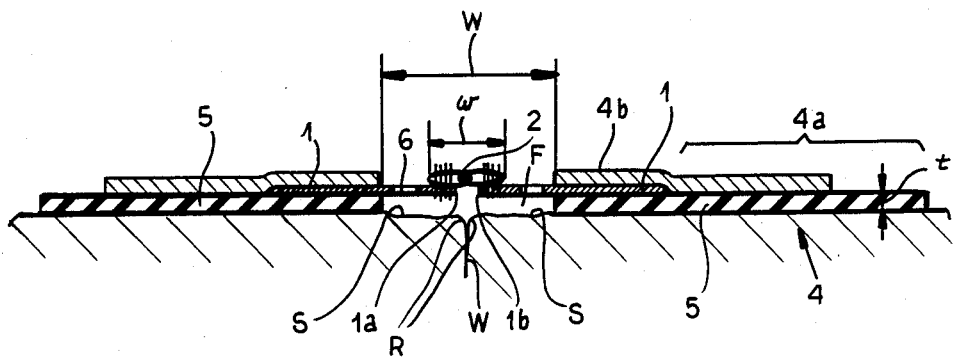
FIG. 2 is a cross—sectional view taken along the line II—II of FIG. 1 and enlarged in scale by comparison to FIG. 1, showing the device as applied to a wound.
Figure 3:
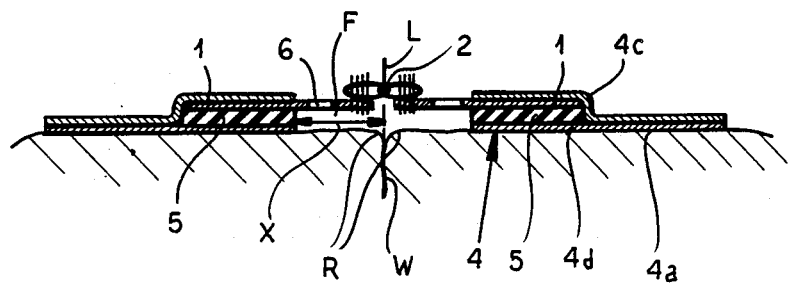
FIG. 3 is a view similar to FIG. 2 but illustrating another embodiment.

From a comparison of FIGS. 1–3 it will be seen that the slide fastener stringer 1, 2, 3 is a conventional garment-type of slide fastener utilized for textile fabrics. It will, according to the invention, make use of low elongatability tapes 1 and coupling elements 2, which, in the coupled state, are buckling free.

From FIGS. 2 and 3, moreover, it will be apparent that on the underside of each tape 1 and spaced from the respective coupling element away from the wound, spacer strips 5 are provided which delimit free spaces F in which the wound lies.

Figure 5:
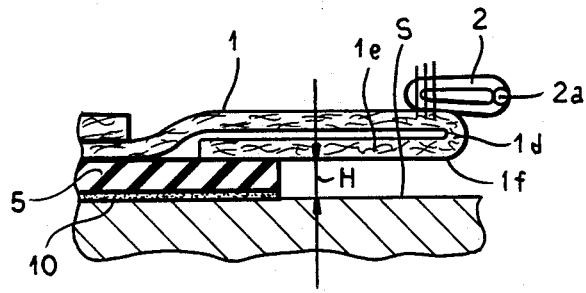
FIG. 5 is a cross-sectional view showing one half of the device of the invention, utilizing the principles of an invisible slide fastener or concealed slide fastener to wound closure.

The device 4 for securing the tapes to the skin S along edges R of the wound W comprise a layer of a pressure adhesive which has been illustrated in the enlarged skin of FIG. 5 at 10 and consists of a hypoallergenic adhesive of the type used in surgical adhesive tape and adhesive plasters. The adhesive strips 4 can be provided with this adhesive layer and can have a portion 4a projecting beyond each tape 1 laterally.

The support tapes 1 are underlain by the adhesive strips 4 at least over a portion of their widths and the adhesive strips 4 have a second contacting region with a width such that they are able to withstand readily the transverse forces generated on closing of the wound by the movement of the slider 3.

By way of example and in a preferred embodiment of the invention, the coupling elements 2 are continuous slide fastener coupling elements, e.g. coils, of a polyamide or polyester synthetic resin monofilament with a thickness of about 0.5 mm. The coupling elements are woven into the support tapes and in the coupling state have a total width w of about 5 mm. The tapes 1 themselves may be woven from polyamide or polyester monofilament or yarn.

The spacing x between each spacing strip 5 and the center line L of the interconnected coupling elements 2 should be between 4 and 10 mm, preferably about 7 mm. The thickness t of the spacing strip should be about 0.5 to 1.5 mm, preferably 1 mm. In the embodiment of FIG. 2, the spacing strip 5 forms one of the adhesive strips and has its underside directly coated with the hypoallergenic adhesive layer. In the embodiment of FIG. 3, each spacer strip 5 is bonded between the adhesive strip and the tape.

Figure 4:
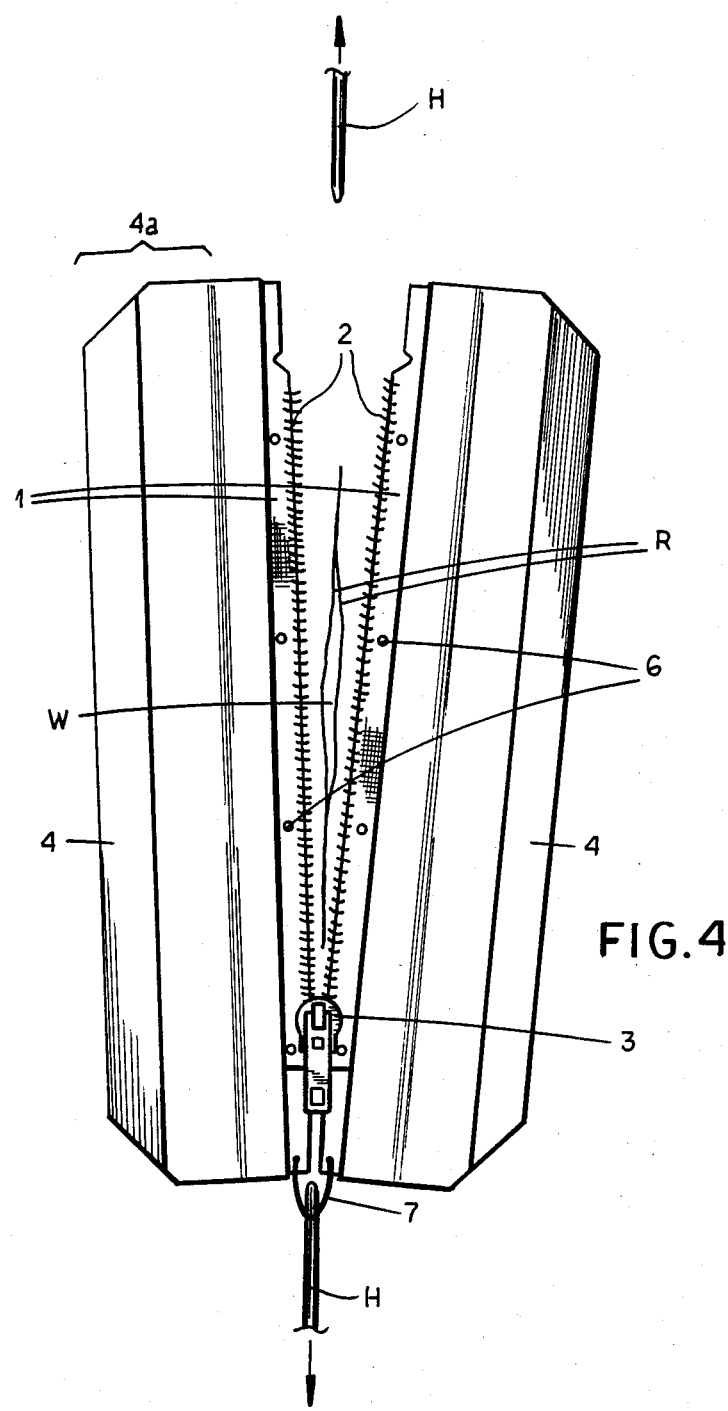
FIG. 4 is an illustration of the application of the device for wound closure.
Figure 6:
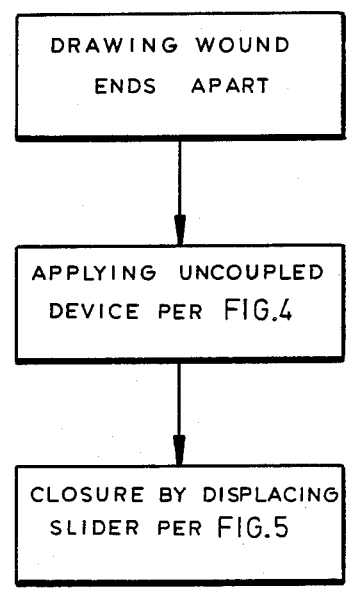
FIG. 6 is a schematic representation of the method steps in applying the wound closing device.

As can be seen especially from FIGS. 1 and 4, the support tapes 1 are provided between the closure elements 2 and the spacer strips 5 with drainage regions which can be spaced apart perforations 6 promoting wound drainage.

In the embodiment represented in FIGS. 1 and 2, the spacer strip 5 is an elastic foam material strip in the form of a microfoam plaster as is widely used in the bandage art. The microfoam preferably is composed of polyvinylchloride cells.

In this embodiment, moreover, a further adhesive layer 4b is provided on top of the tape 1 and extending onto the adhesive layer 5. This additional cover layer also can be composed of a foam material adhesive strip.

It may be said with respect to FIGS. 1 and 2 that in this embodiment the spacer strip 5 forms one of the adhesive strips 4 or beyond the spacer region, becomes the spacer strip 4. By contrast, in the embodiment of FIG. 3, the spacer strip 5 is disposed between two adhesive strips 4c and 4d, at least the lowermost of which is a strip composed of adhesive gauze or surgical cotton coated with a pressure adhesive and of low extensibility in the longitudinal direction but a higher degree of extensibility or stitch in the transverse direction. In the embodiment illustrated, the strips 4 are secured to the tapes 1 by adhesive bonding, although the other attachment techniques described can also be used.

From FIG. 1 it can be seen that the closed end of the slide fastener is provided with a holding loop 7 which can be gripped by the user when the slider is moved upwardly to close the wound.

In operation, a gaping surgical wound W may be drawn closed by the use of single-prong hooks H, for example, pulling on the wound in the longitudinal direction oppositely to cause the wound edges R to approximate one another and thus reduce the area of the wound.

With the wounds thus narrowed, the device is applied so that the spacing of the wound edge R from the edge of the spacing strip 5 is approximately half the width W of the free space F.

With the loop 7 held by forceps, for example, the slider is drawn upwardly (FIG. 4) to pull the edges R of the wound together.

If one now turns to FIG. 5, one can see that the height H of the free space is determined by the spacer strip 5 with the adhesive coating 10 on its underside, but that the coupling element 2 with its coupling head 2a is held even further away from the skin S because the tape 1 is provided with a fold 1d about a longitudinal axis so that the added thickness 1e of this fold forms the spacer or contributes to the spacing of the coupling element from the skin together with spacer 5. A coating 1f of silicone can be provided on the skin side of the tape. To facilitate fastening of the device to the skin, a masking layer of paper or the like may be provided on the sterile packaged device and may be stripped away to expose the adhesive which can be pressed against the skin as in conventional surgical bandages.

I claim:

1. A device for closing a wound in the body of a subject, especially a linear surgical incision, comprising:
   a pair of low-extensibility garment-type flexible textile support tapes having juxtaposed inner edges;
   respective continuous flexible garment-type slide-fastener coupling elements affixed to said tapes along said edges and having mutually interdigitatable coupling heads composed of polyester or polyamide and compression and buckling resistant when coupled together;
   a slider shiftable along said coupling elements for selectively interdigitating the coupling heads of said coupling elements to couple said elements together and separating said coupling elements;
   a respective spacer strip fixed on a surface of each tape, said surface facing toward said body and said strip spaced from the respective coupling element for holding said coupling elements away from said wound; and
   means for adhesively bonding said tapes to said body on opposite sides of said wound with said spacer strips interposed between said tapes and said body, said means including an adhesive layer having a hypoallergenic adhesive facing toward and contacting said body, and at least one adhesive strip overlapping each of said tapes and having a portion projecting beyond an outer edge of the respective tape opposite the respective inner edge, the widths of said adhesive strips including the projecting portions thereof being at least sufficient to enable the bond between said tapes and said body to withstand the wound-closing force between opposite sides of the wound.

2. The wound-closing device defined in claim 1 wherein said coupling elements are continuous coupling elements composed of polyamide or polyester.

3. The wound-closing device defined in claim 2 wherein said continuous coupling elements are formed form polyamide or polyester monofilament having a thickness of at most 0.5 mm.

4. The wound-closing device defined in claim 2 wherein said coupling elements are anchored in the respective tapes by weaving the coupling elements into the fabric of said tapes.

5. The wound-closing device defined in claim 2 wherein said coupling elements have, when coupled together, a combined width of about 5 mm.

6. The wound-closing device defined in claim 2 wherein said tapes are composed of polyamide or polyester.

7. The wound-closing device defined in claim 2 wherein said spacer strips are each spaced from a centerline of the interdigitated coupling elements by substantially 4 to 10 mm.

8. The wound-closing device defined in claim 7 wherein said spacer strips are each spaced from said centerline by about 7 mm.

9. The wound-closing device defined in claim 7 wherein said spacer strips have thicknesses of about 0.5 to 1.5 mm.

10. The wound-closing device defined in claim 9 wherein said spacer strips have thicknesses of about 1 mm.

11. The wound-closing device defined in claim 2 wherein said adhesive layer is applied to a ski side of each of said spacer strips.

12. The wound-closing device defined in claim 2, further comprising means in at least one of said tapes between a respective one of said coupling elements and the respective spacer strip for permitting draining of said wound.

13. The wound-closing device defined in claim 12 wherein said means for permitting draining of said wound include perforations formed in said tapes.

14. The wound-closing device defined in claim 2 wherein said spacer strips are elastic adhesive strips of foamed material in the form of microfoam adhesive plasters wherein the foamed material includes closed polyvinylchloride or polyethylene cells.

15. The wound-closing device defined in claim 2 wherein said adhesive strips are surgical cotton strips having adhesive undersides and of transverse extensibility, but longitudinally limited extensibility.

16. The wound-closing device defined in claim 2 wherein said tapes and said adhesive strips are bonded together by welding.

17. The wound-closing device defined in claim 2 wherein said tapes and said adhesive strips are bonded together by adhesive bonding.

18. The wound-closing device defined in claim 2 wherein said tapes and said adhesive strips are bonded together by adhesive bonding.

19. The wound-closing device defined in claim 2 wherein said tapes and said adhesive strips are secured together at least in part by stitched seam sewing.

20. The wound-closing device defined in claim 2 wherein said tapes and said adhesive strips are secured together at least in part by stitched basting.

21. The wound-closing device defined in claim 2 wherein said coupling elements are secured together at an end of the device, said device further comprising a holding loop secured to said tapes at one of the ends of the device for gripping of the device during movement of said slider along said coupling elements for taking up longitudinal forces generated in the coupling and decoupling of said coupling elements by said slider.

22. The wound-closing device defined in claim 2 wherein said tapes are planar bands lying in a common plane and said tapes extend below said coupling elements.

23. The wound-closing device defined in claim 2 wherein a longitudinal axis runs parallel to a major length of said coupling elements and said tapes are each folded in the region of the respective coupling element about said longitudinal axis to a U-shape in cross section to form a fold, the respective coupling element is mounted on the fold, and the fold at least contributes to spacing of the coupling elements away from the body.

24. A method of closing a gaping surgical-incision wound flanked by skin of a body of a patient, said method comprising the steps of:
  (a) initially drawing ends of the wound apart longitudinally of the wound to cause longitudinal edges of the wound to be approached to one another;
  (b) while said ends of the wound are drawn apart in step (a) adhesively applying to said body of the patient a device for closing said wound in an uncoupled state thereof, said device including:
    a pair of low-extensibility garment-type flexible textile support tapes having juxtaposed inner edges,
    respective continuous flexible garment-type slide-fastener coupling elements affixed to said tapes along said edges and having mutually interdigitatable coupling heads composed of polyester of polyamide and compression and buckling resistant when coupled together,
    a slider shiftable along said coupling elements for selectively interdigitating the coupling heads of said coupling elements to couple said elements together and separating said coupling elements,
    a respective spacer strip fixed on a surface of each tape, said surface facing toward said body of the patient and said strip spaced from the respective coupling element for holding said coupling elements away from said wound over a free space adapted to extend the length of said wound, and
    means for adhesively bonding said tapes to said body of the patient on opposite sides of said wound with said spacer strips interposed between said tapes and said body of the patient, said means including an adhesive layer having a hypoallergenic adhesive facing toward and contacting said body of the patient, and at least one adhesive strip overlapping each of said tapes and having a portion projecting beyond an outer edge of the respective tape opposite the respective inner edge, the widths of said adhesive strips including the projecting portions thereof being at least sufficient to enable the bond between said tapes and said body of the patient to withstand the wound-closing force between opposite sides of the wound, said tapes and spacer strips being applied to the skin of the body of the patient so that the distance between each wound edge and the respective spacer strip is substantially half of the width of said free space; and
  (c) displacing said slider along said coupling elements to effect interdigitation of said coupling elements and draw the wound edges which have been approached to one another into wound-knitting contact with one another along the length of the wound.

25. The method defined in claim 24 wherein said device forms a slide fastener which is approximately 4 cm longer than said wound, said device being positioned on the skin of the body of the patient so as to extend by about 2 cm beyond each end of the wound.

* * * * *